United States Patent
Ur

(10) Patent No.: US 10,803,296 B2
(45) Date of Patent: Oct. 13, 2020

(54) AUTOMATIC SCENT SELECTION

(71) Applicant: Shmuel Ur Innovation Ltd, Shorashim (IL)

(72) Inventor: Shmuel Ur, Shorashim (IL)

(73) Assignee: SHMUEL UR INNOVATION LTD., Shorashim (IL)

( * ) Notice: Subject to any disclaimer, the term of this patent is extended or adjusted under 35 U.S.C. 154(b) by 341 days.

(21) Appl. No.: 15/120,247

(22) PCT Filed: Apr. 13, 2015

(86) PCT No.: PCT/IL2015/050393
§ 371 (c)(1),
(2) Date: Aug. 19, 2016

(87) PCT Pub. No.: WO2015/145452
PCT Pub. Date: Oct. 1, 2015

(65) Prior Publication Data
US 2017/0098121 A1    Apr. 6, 2017

(30) Foreign Application Priority Data
Mar. 24, 2014    (IL) .......................................... 231686

(51) Int. Cl.
*G06K 9/00* (2006.01)
*A45D 34/00* (2006.01)
(Continued)

(52) U.S. Cl.
CPC ......... *G06K 9/00288* (2013.01); *A45D 34/00* (2013.01); *A61L 9/125* (2013.01); *B05B 9/03* (2013.01); *B05B 12/122* (2013.01); *B05B 12/14* (2013.01); *B05B 15/62* (2018.02); *G06K 9/00671* (2013.01); *A61L 2209/111* (2013.01); *A63J 2005/008* (2013.01)

(58) Field of Classification Search
CPC ..................... G06K 9/00288; G06K 9/00671; A61L 9/125; A61L 2209/111; B05B 15/62; B05B 9/03; B05B 12/122; B05B 12/14; A45D 34/00; A63J 2005/008
USPC .................................................. 700/231–244
See application file for complete search history.

(56) References Cited

U.S. PATENT DOCUMENTS 4,374,571 A * 2/1983 Hirvela ..................... A61L 9/12
                                                                     206/0.5
7,809,601 B2 * 10/2010 Shaya .................... G06Q 30/02
                                                                     700/233
(Continued)

FOREIGN PATENT DOCUMENTS

CN    103493597 A    1/2014
EP    2369900 A1    9/2011

OTHER PUBLICATIONS

ISR for PCT/IL2015/050393 (dated Aug. 5, 2015).
Third Office Action in CN 201580015549.0 (dated Oct. 24, 2019).

*Primary Examiner* — Michael Collins

(57) ABSTRACT

A computer implemented method, a computerized apparatus and a computer program product for automatic scent selection. The computer implemented method comprising: detecting an event, wherein the event is associated with a user. The method further comprising: in response to the detection of the event, determining, by a processor, a scent for the event. The method further comprises applying, by a dispenser, the selected scent on the user.

22 Claims, 4 Drawing Sheets

(51) Int. Cl.
*B05B 15/00* (2018.01)
*B05B 9/03* (2006.01)
*B05B 12/12* (2006.01)
*B05B 12/14* (2006.01)
*A61L 9/12* (2006.01)
*B05B 15/62* (2018.01)
*A63J 5/00* (2006.01)

(56) References Cited

U.S. PATENT DOCUMENTS

| | | | | |
|---|---|---|---|---|
| 8,457,695 B2* | 6/2013 | Hwang | ............ | H04M 1/21 455/575.1 |
| 8,948,839 B1* | 2/2015 | Longinotti-Buitoni | ............ | A61B 5/6804 29/825 |
| 9,931,425 B2* | 4/2018 | Edwards | ............ | A61L 9/032 |
| 10,078,842 B2* | 9/2018 | Ur | ............ | G05B 15/02 |
| 10,254,260 B2* | 4/2019 | Amin | ............ | G01N 33/0031 |
| 10,592,510 B2* | 3/2020 | Amin | ............ | G01N 33/0031 |
| 2005/0079143 A1* | 4/2005 | Betz | ............ | A45D 40/04 424/65 |
| 2007/0099804 A1* | 5/2007 | Fadel | ............ | C11D 3/50 510/101 |
| 2009/0091470 A1* | 4/2009 | Yu | ............ | A63H 3/28 340/12.15 |
| 2010/0155414 A1* | 6/2010 | Hu | ............ | A01M 1/2038 222/1 |
| 2011/0226864 A1* | 9/2011 | Kim | ............ | H04M 1/72597 239/6 |
| 2011/0268605 A1* | 11/2011 | Haran | ............ | A61L 9/122 422/4 |
| 2012/0018528 A1* | 1/2012 | Samain | ............ | H04L 67/125 239/6 |
| 2014/0266604 A1* | 9/2014 | Masood | ............ | G06K 9/00221 340/5.83 |
| 2014/0333415 A1* | 11/2014 | Kursun | ............ | G06F 21/32 340/5.83 |
| 2015/0048178 A1* | 2/2015 | Edwards | ............ | A61L 9/032 239/13 |
| 2017/0067608 A1* | 3/2017 | Patton | ............ | F21S 10/046 |
| 2017/0070845 A1* | 3/2017 | Edwards | ............ | B05B 7/0081 |

* cited by examiner

AUTOMATIC SCENT SELECTION

CROSS-REFERENCE TO RELATED APPLICATION

This application claims the benefit of Israeli Patent Application No. 231686 filed Mar. 24, 2014, entitled "Automatic scent selection", which is hereby incorporated by reference in its entirety for all purposes.

TECHNICAL FIELD

The present disclosure relates to scent dispensers.

BACKGROUND

Smell is one of the strongest and most primal of all the human senses. Many researches shows that smell can influence human thoughts and behavior more than expected. Just like verbal, dress and physical cues, scent, may help people to convey impression and sometimes influence the way people perceive each other.

In perfumery, notes are descriptors of scents. Notes are generally separated into three classes: top notes, middle notes and base notes. The classes denote groups of scents that may be smelled with respect to the time after the perfume application. A top note scent may be a scent that is perceived immediately or within a short time after application of a perfume. A top note scent may typically consist of relatively small and light molecules. The top note may be characterized by a relatively noticeable scent. The top note may be of high volatility (e.g., evaporation coefficient of about 1 to about 14). The top note may be fast evaporating, such as within approximately seconds of dispensing. The top note may be suitable for conveying a desired initial impression to others.

The perfume industry is pushing the wealth of the scent world to practically every aspect of everyday life and successfully spreading into hospitality, retail, consumer packaged goods, beauty, healthcare, real estate and other worldwide marketplaces.

Emerging scent applications, such as digitally transmitting and receiving scent, are becoming more affordable and therefore more available in the consumer marketplace. One popular example is delivering a specific scent for enhancing videogame experience. Artificial recreation of a smell by synthesizing chemical molecules is one enabling technology of these scents on demand applications.

BRIEF SUMMARY

One exemplary embodiment of the disclosed subject matter is a method comprising: detecting an event, wherein the event is associated with a user; in response to the event, determining, by a processor, a scent for the event; and applying the scent on the user.

Another exemplary embodiment of the disclosed subject matter is a system comprising: a detecting component configured to detect an event associated with a user; a scent determinator configured to determine a scent for the event; and a dispenser configured to apply the scent on the user.

Yet another exemplary embodiment of the disclosed subject matter is a perfume cartridge comprising a container holding a perfume, wherein the cartridge is configured in size and shape to be loaded to a perfume dispensing device, wherein the perfume dispensing device is configured to dispense the perfume from the cartridge, wherein the perfume dispensing device is adapted in size and shape to accommodate multiple perfume cartridges.

THE BRIEF DESCRIPTION OF THE SEVERAL VIEWS OF THE DRAWINGS

The present disclosed subject matter will be understood and appreciated more fully from the following detailed description taken in conjunction with the drawings in which corresponding or like numerals or characters indicate corresponding or like components. Unless indicated otherwise, the drawings provide exemplary embodiments or aspects of the disclosure and do not limit the scope of the disclosure. In the drawings.

DETAILED DESCRIPTION

Figure 1:
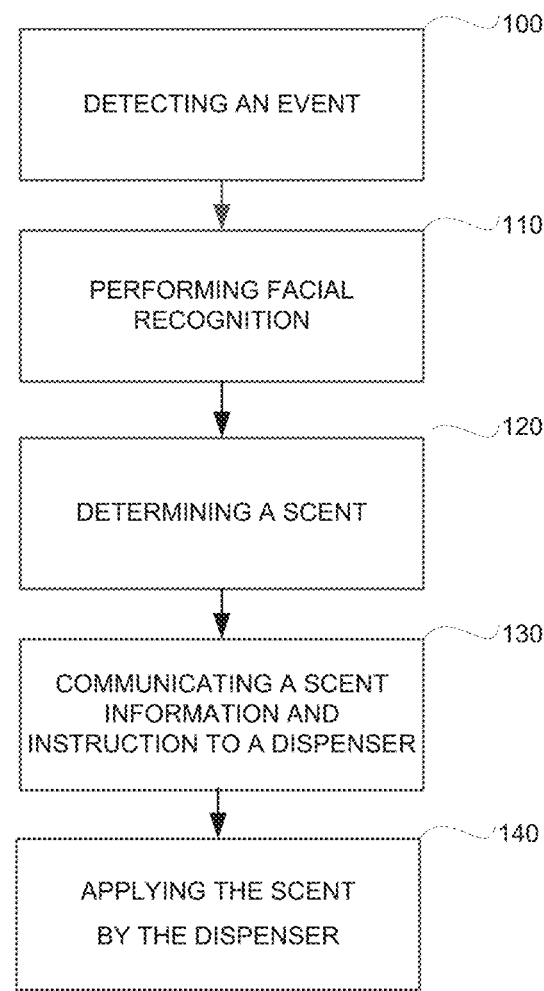
FIG. 1 shows a flowchart diagram of a method, in accordance with some exemplary embodiments of the disclosed subject matter.

The disclosed subject matter is described below with reference to flowchart illustrations and/or block diagrams of methods, apparatus (systems) and computer program products according to embodiments of the subject matter. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowchart and/or block diagram block or blocks.

One technical problem dealt with by the disclosed subject matter is to automatically personalize a scent of a user based on an event or the person the user is about to encounter. People may wish to use different perfume for each person they meet and the type of events they encounter throughout the day. Replacing a perfume every few hours or twice a day may not fulfill social needs of the user throughout the day. Additionally or alternatively, a compact and efficient manner to personalize a scent worn by a user may also be desired in view of the growing awareness of the impact smell has on the way people are perceived by others.

One technical solution is determining an appropriate scent for an event that is associated with the user and applying the scent on the user. In some exemplary embodiments, facial recognition may be employed to allow personalization of the scent based on identity or other characteristics of a person that the user is about to encounter. The disclosed subject matter may utilize a dispenser, capable of applying the appropriate scent for the event. An event may be, for example, a detection of a gesture by the user, an identification of a smell, an identification of a location, a facial recognition, a volitional action of the user, a combination thereof, or the like. The characterization of an event may be, for example, characterizing a person such as a gender of the person, an identity of the person, an age of the person, a demographic profile of the person, or the like; type of a place; time of a day; a combination thereof, or the like. a combination thereof, or the like. Additionally or alternatively, characterization of an event may be based on a type of relationship between the user and a person in a social network such as for example Facebook™, Twitter™, Linkedin™ or the like.

In some embodiments, the disclosed subject matter may recognize an approaching person and utilize a facial recognition module to characterize the approaching person. A scent can be selected and applied on the user prior to the user meeting the approaching person. As an example, a perfume may be applied on the wrist of the user, just in time before the forthcoming handshake with the approaching person. In some exemplary embodiments, the timing in which the scent is applied may be based upon the distance and the movement direction of the approaching person. Additionally or alternatively, the scent may be applied based on a gesture which is part of a non-verbal greeting between the user and the approaching person, such as for example the user extending his hand for a handshake or spreading his hands to hug the approaching person.

In some embodiments, the dispenser may be a fast release dispenser. In some embodiments, the dispenser may be a fast release dispenser configured to apply a specific perfume from a plurality of perfume cartridges. Each one of the perfume cartridges may be associated with specific event. Additionally or alternatively, the dispense may be operatively coupled to a scent synthesizer configured to synthesize a scent on-demand.

In some exemplary embodiments, the dispenser may dispense fast evaporating perfume which may evaporate relatively fast and will not interfere with another scent, should it be applied later on. Fast evaporating perfume may enable use of the disclosed subject matter to provide for an on-demand personalized scent which may be modified on demand and relatively frequently.

One technical effect of utilizing the disclosed subject matter is equipping the user with automatic device capable to personalize the scent of the user. In some exemplary embodiments, the user may be enabled to convey different impression to different people, in different location, or at different time, by using different scents. The user may use one fragrance suitable for a romantic meeting and another for a business meeting.

Another technical effect of utilizing the disclosed subject matter is providing retail businesses, such as an eclectic department store, with automatic scent selecting device to improve the performance of the salesmen, wherein the selection of the scent is based on customer's profiling. Upon characterizing the customer's profile, such as the customer's buying habits, an appropriate scent may be applied on the salesperson who will interact with the customer. The scent may be selected so as to improve the salesmanship of the salesperson with respect to the customer. As an example, different scents may be used to convey different messages to the customer, such as one scent may be used to increase the reliability of the salesperson while another scent may be used to encourage purchase of more luxurious items.

Referring now to FIG. 1, showing a flowchart diagram of a method in accordance with some exemplary embodiments of the disclosed subject matter.

In Step 100, an event may be detected. The event may be used to trigger the system to select and apply a specific scent on the user. A detecting component such as 220 of FIG. 2 may be utilized to detect the event. In some exemplary embodiments, the event may be a gesture by the user. Additionally or alternatively, the event may an identification of smell. Additionally or alternatively, the event may be arriving at a predetermined location. Additionally or alternatively, the event may be identifying an approaching person approaching to the user. In some exemplary embodiments, the event may be a verbal greeting and nonverbal greeting such as for example, a handshake, a hug, a combination thereof, or the like. In some exemplary embodiments, an event may be a part of a non-verbal greeting, such as for example, when the user stretches his or her arm with an intention to shake the hand of an approaching person. Additionally or alternatively, the detecting component may be configured to indicate an event if, for example, the detecting component is recognizing a forthcoming or potential physical contact with a person.

In Step 110, facial recognition may be performed. The facial recognition may be performed by a facial recognition component, such as 230 of FIG. 2, operatively coupled with a camera, such as 252 of FIG. 2. The facial recognition may determine characterizations of a person such as a gender of the person, an identity of the person, an age of the person, a demographic profile of the person, a relationship with the person a combination thereof, or the like. In some exemplary embodiments, the facial recognition may be performed to characterize a plurality of people. Additionally or alternatively, the facial recognition may be performed to detect an approaching person and estimate the time to encounter that person based on the distance and direction between the user and the person.

In Step 120, a scent may be determined. The scent determination may be performed by a scent determinator such as 240 of FIG. 2. The determination of the scent may be based predefined rules. In some exemplary embodiments, the rules may be defined by the user. As an example, the rules may define a different scent in response to different event types, to different characterization of people, or the like. In some exemplary embodiments, event of different types may trigger different scents. As an example, different gestures may trigger different scent selection. As another example, a different scent may be selected in response to an event which involves meeting a person. The scent may be, for example, selected based on characterization of the person (e.g., such as determined in Step 110)

Figure 2:
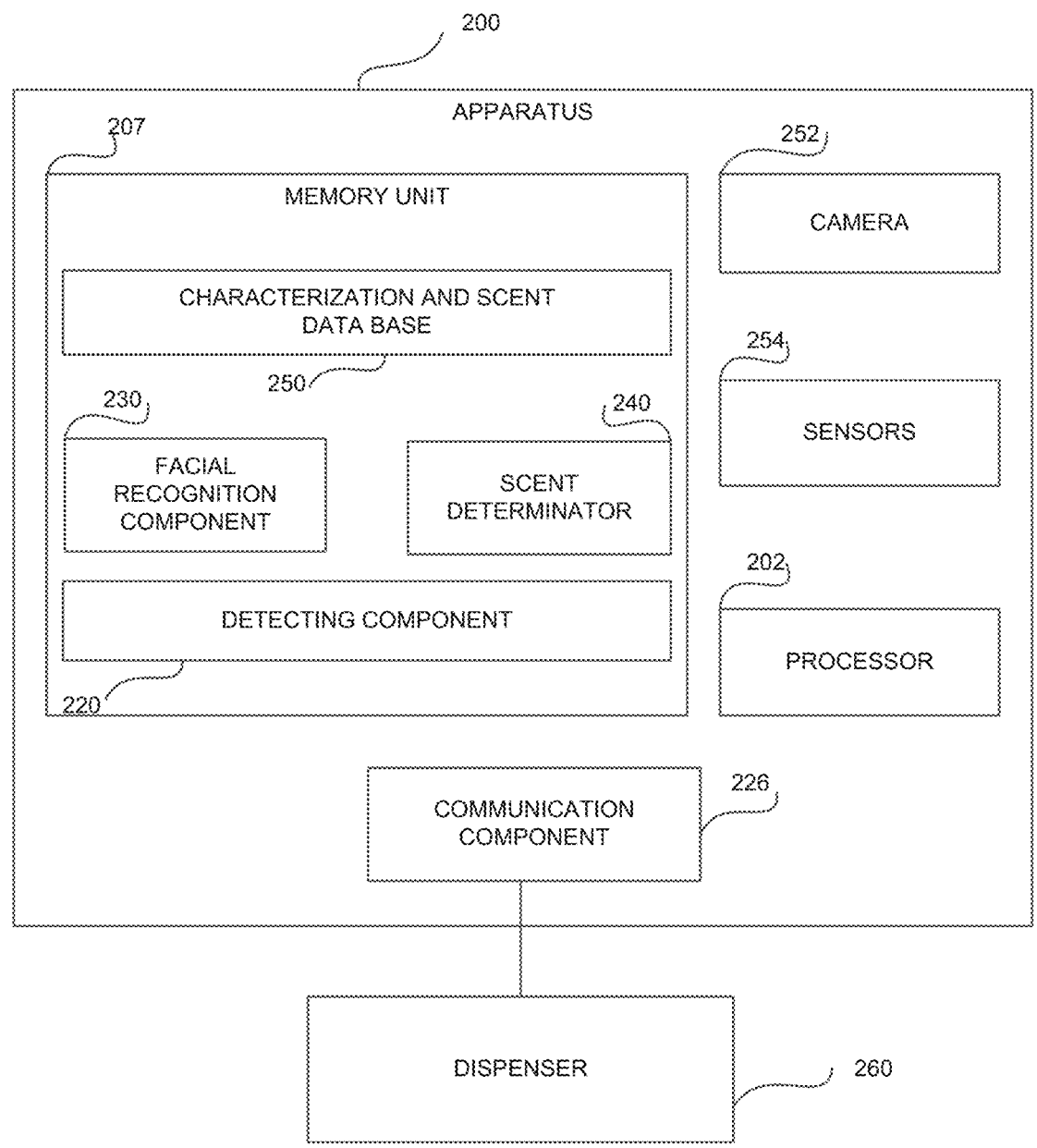
FIG. 2 shows a block diagram of a system, in accordance with some exemplary embodiments of the disclosed subject matter.

In some exemplary embodiments, the scent determination may be based on a characterization and scent data base, such as 250 of FIG. 2. The data base may comprise set of rules defined by the user for associating the scent to an event type or properties thereof. As an example, the rules may define a first scent to be selected in response to meeting the user's spouse, a second scent to be selected in response to meeting a woman, and a third scent to be selected in response to meeting men of estimated high demographic background. Additionally or alternatively, the scent determination may be based on social connectivity between the user and a person in a social network such as for example Facebook™, Twitter™, Linkedin™ or the like.

In some exemplary embodiments, the determination of Step 120 may result in a selection of a specific scent to be applied in response to the event. Additionally or alternatively, Step 120 may determine a duration in which the scent is to be dispensed.

In some exemplary embodiments, the determined scent may be selected based on availability of perfumes. As an example, in case a perfume cartridge is depleted a replacement scent may be used instead.

In some exemplary embodiments, the determined scent may be a top note. The scent may be selected from available top note scents or from potentially synthesizable top note scents.

In Step 130, dispensing instruction may be communicated to a dispenser, such as 240 of FIG. 2. The instruction may indicate the selected scent of Step 120. In some exemplary embodiments, information may be communicated in addition to the selected scent, such as for example a dispensing duration, an instruction to synthesize the scent, an instruction to apply the scent, a duty cycle of reapplying the scent, or the like. The communicated instruction may be communicated via wired communication, wireless communication, or the like.

In Step 140, the scent may be applied by a dispenser. In some exemplary embodiments, the dispenser may apply a fast evaporating scent on the user. In some exemplary embodiments, the dispenser may be configured to perform real time synthesis of the selected scent. In some embodiments, the dispenser may be configured to apply a specific perfume from a plurality of perfume cartridges. Each one of the perfume cartridges may be associated with specific event.

Referring now to FIG. 2, showing a block diagram of a system in accordance with some exemplary embodiments of the disclosed subject matter. An Apparatus 200 may be a computerized apparatus adapted to perform methods such as depicted in FIG. 1.

In some exemplary embodiments, Apparatus 200 may comprise a Processor 202. Processor 202 may be a Central Processing Unit (CPU), a microprocessor, an electronic circuit, an Integrated Circuit (IC) or the like. Additionally or alternatively, Apparatus 200 can be implemented as firmware written for or ported to a specific processor such as Digital Signal Processor (DSP) or microcontrollers, or can be implemented as hardware or configurable hardware such as field programmable gate array (FPGA) or application specific integrated circuit (ASIC). Processor 202 may be utilized to perform computations required by Apparatus 200 or any of it subcomponents.

In some exemplary embodiments of the disclosed subject matter, Apparatus 200 may comprise a Communication Component 226. Apparatus 200 may utilize Communication Component 226 as an interface to transmit and/or receive information and instructions between Apparatus 200 and external I/O devices, such as a Dispenser 260 or the like.

In accordance with some exemplary embodiments of the disclosed subject matter, Apparatus 200 may comprise a Camera 252. In some exemplary embodiments, Camera 252 may be an integral part of an augmented reality glasses worn by the user; an integral part of a mobile device, such as a cellular phone; a standalone camera; webcam; or the like.

In accordance with some exemplary embodiments of the disclosed subject matter, Apparatus 200 may comprise Sensors 254. Sensors 254 may be utilized for detecting an event as depicted in steps 100 of FIG. 1. In some exemplary embodiments, Detecting Component 220 may utilize Sensors 254 to detect events. In some exemplary embodiments, Sensors 254 may comprise a scent sensor, a location sensor, a gesture sensor, a camera such as Camera 252, a voice command sensor, or the like. The Sensors 254 may be an integral part of an augmented reality glasses worn by the user.

In some exemplary embodiments, Sensors 254 may comprise a scent sensor. The scent sensor may be a device capable of recognizing a smell. The scent sensor may be utilized to identify an event upon recognition of a specific smell such as for example a smell of cigarettes smoke, or the like.

In some exemplary embodiments, Sensors 254 may comprise a location sensor. The location sensor may be a device such as an Indoor Positioning System (IPS) for indoor tracking, a Global Positioning System (GPS) for outdoor tracking, Multilateration device, or the like. In some exemplary embodiments, the location sensor may be utilized to identify an event upon tracking the user entry to a location, such as, for example, a public restroom. In some exemplary embodiments, the location sensor may be configured to detect an event when the user arrives at a designated destiny, such as, for example, a restaurant.

In some exemplary embodiments, Sensors 254 may comprise a gesture sensor. The gesture sensor may utilize a proximity sensor, a motion detector, a camera, or the like, in order to detect a gesture. In some exemplary embodiments, the gesture sensor may be utilized to detect movement of hands, head, or other parts of the user's body to indicate an incoming gesture event.

In some exemplary embodiments, Sensors 254 may be configured to recognize the user's intentional instruction to apply the scent. In some exemplary embodiments, the user's intentional instruction may be: touching a predetermined part of the augmented reality glasses, touching a touchpad, providing a voice command, pressing a button, or the like.

In some exemplary embodiments, Apparatus 200 may comprise a Memory Unit 207. Memory Unit 207 may be persistent or volatile. For example, Memory Unit 207 can be a Flash disk, a Random Access Memory (RAM), a memory chip, an optical storage device such as a CD, a DVD, or a laser disk; a magnetic storage device such as a tape, a hard disk, storage area network (SAN), a network attached storage (NAS), or others; a semiconductor storage device such as Flash device, memory stick, or the like. In some exemplary embodiments, Memory Unit 207 may retain program code to activate Processor 202 to perform acts associated with any of the steps shown in FIG. 1.

The components detailed below may be implemented as one or more sets of interrelated computer instructions, executed for example by Processor 202 or by another processor. The components may be arranged as one or more executable files, dynamic libraries, static libraries, methods, functions, services, or the like, programmed in any programming language and under any computing environment.

A Detecting Component 220 may be configured to detect an event associated with a user. In some exemplary embodiments, the Detecting Component 220 may be operatively coupled with Sensors 254. The events detected by Detecting Component 220 may be based on a gesture, smell recognition, an arrival of the user to a location, a volitional action of the user, a voice command, a handshake, a hug, or the like. In some exemplary embodiments, Detecting Component 220 may detect a gesture event if for example stretching motion an arm forward may be in some exemplary embodiments an indication of a forthcoming handshake event. Additionally or alternatively, Detecting Component 220 may detect, using Facial Recognition Component 230, an event in which a person, such as a friend, a social relationship of the user, or the like, that is near the user or approaching the user.

A Facial Recognition Component 230 may be configured to perform facial recognition. The Facial Recognition Component 230 may be operatively coupled with Camera 252. In some exemplary embodiments, Facial Recognition Component 230 may be utilized to characterize a person. A person may be characterized by gender, identity, age, demographic profile, a combination thereof, or the like. Additionally or alternatively, Facial Recognition Component 230 may be utilized in detecting an event of an person approaching to the user.

A Scent Determinator 240 may be configured to determine the scent. In some exemplary embodiments, the Scent Determinator 240 may obtain event information from Detecting Component 220, characterization information from Facial Recognition Component 230, a combination thereof, or the like. In some exemplary embodiments, the Scent Determinator 240 may utilize a Characterization and Scent Data Base (CSDB) 250 to determine the scent based on the event and characterization information. Additionally or alternatively, the Scent Determinator 240 may instruct a dispenser such as Dispenser 260 to apply the selected scent on the user.

Memory Unit 207 may retain CSDB 250. In some exemplary embodiments, CSDB 250 may be a database which comprises rules for scent selection. The rules may define a scent to be selected based on event properties, such as a characterization of a person. In some exemplary embodiments, the user may define the rules in CSDB 250. In some exemplary embodiments, Scent Determinator 240 may utilize CSDB 250 for determining the scent.

As an example, CSDB 250 may retain a record corresponding to a rule of selecting PERFUME 1 for a person characterized as a young woman and another record corresponding to a rule of selecting PERFUME 5 for a person characterized as old man. CSDB 250 may also retain a record corresponding to a rule of selecting PERFUME 3 for the spouse of the user.

In accordance with some exemplary embodiments of the disclosed subject matter, a Dispenser 260 may be used. Dispenser 260 may be a fast release dispenser. Dispenser may be utilized to perform Step 140 of FIG. 1. In some exemplary embodiments, Dispenser 260 may receive instruction to apply a scent from the Scent Determinator 240 trough Communication Component 226. In some exemplary embodiments, the instruction may include the selected scent to be applied. In some exemplary embodiments, Dispenser 260 may comprise a scent synthesizer for synthesizing the selected scent on demand. In some embodiments, the dispenser may comprise a plurality of perfume cartridges, wherein Dispenser 260 may apply the perfume from the cartridge associated with the event. In some exemplary embodiments, Dispenser 260 may be physically separated from Apparatus 200 and may be worn on the user's body independently from Apparatus 200. In some exemplary embodiments, the Dispenser 260 may be integrated into a wearing item such as for example an augmented reality glasses, a bracelet, a tie, a cufflink, a scarf, a jewelry pin, a necklace, or the like. In some exemplary embodiments, Dispenser 260 may be an integral part Apparatus 200. As an example Apparatus 200 may be implemented together with Dispenser 260 within augmented reality glasses, such as those shown in FIG. 3A.

In some exemplary embodiments, scents of top note class may be used by Dispenser 260. Top note scents may be perceived right after application of the perfume. Top note scents may typically consist of small and light molecules and may be characterized by noticeable scent, volatility and fast evaporation. Top note scents may be used to convey a desired impression. In some exemplary embodiments, as the top note scents may evaporate relatively fast, application of another scent that may occur within several minutes or even dozen of seconds, would not be disturbed by the previously applied top note scent.

Figure 3A:
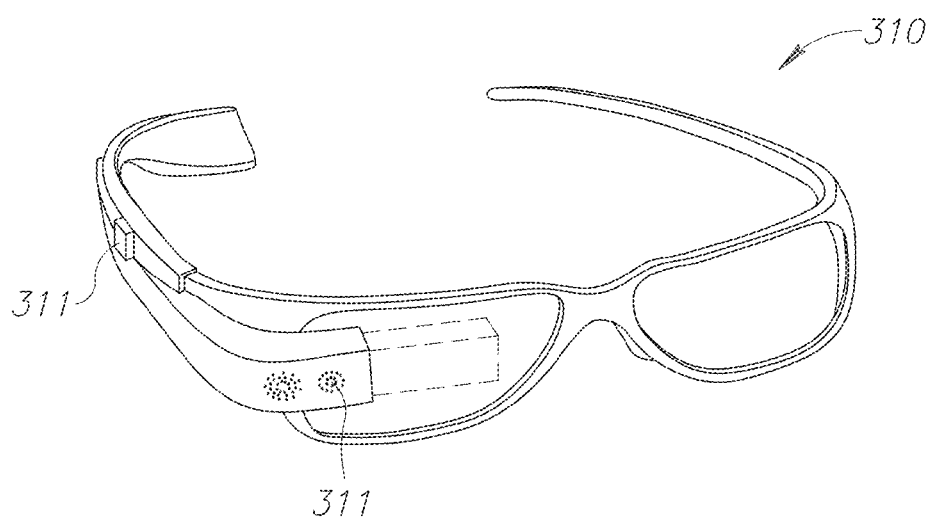
FIG. 3A illustrates augmented reality glasses, in accordance with some exemplary embodiments of the disclosed subject matter.

Referring now to FIG. 3A, showing an augmented reality glasses, in accordance with some exemplary embodiments of the disclosed subject matter.

In some exemplary embodiments, an Augmented Reality Glasses 310 may be used. The Augmented Reality Glasses 310 may comprise an apparatus such as Apparatus 200 of FIG. 2, a Dispenser 311, a Camera 312, a combination thereof, or the like. In some exemplary embodiments Dispenser 311 may be dispensing a Scent 317.

Figure 3B:
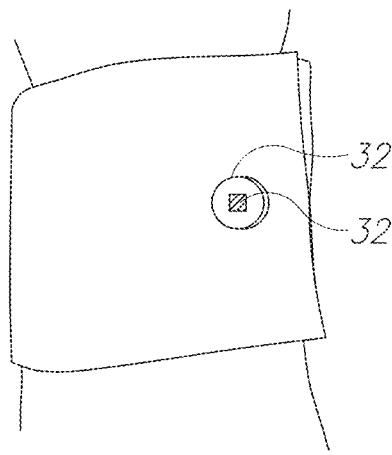
FIG. 3B-3D show illustrations of dispensers, in accordance with some exemplary embodiments of the disclosed subject matter.

Referring now to FIG. 3B, showing a dispenser embedded within a cufflink, in accordance with some exemplary embodiments of the disclosed subject matter. Dispenser 325 may be used as a part of a cufflink 320 to apply scent on the user's wrist.

Figure 3C:
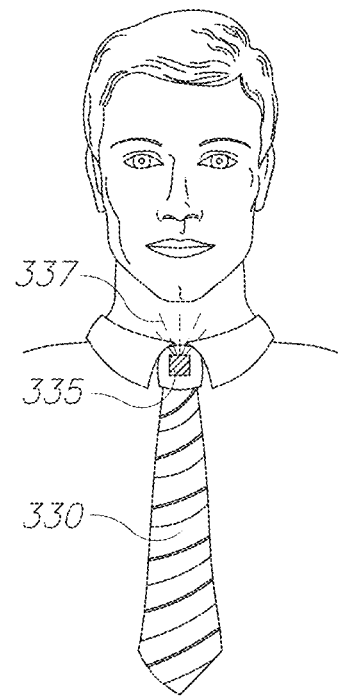

Referring now to FIG. 3C, showing a dispenser embedded within a tie, in accordance with some exemplary embodiments of the disclosed subject matter. Dispenser 335 may be used as a part of a Tie 330 to apply scent, such as, Scent 337 on the user's neck.

Figure 3D:
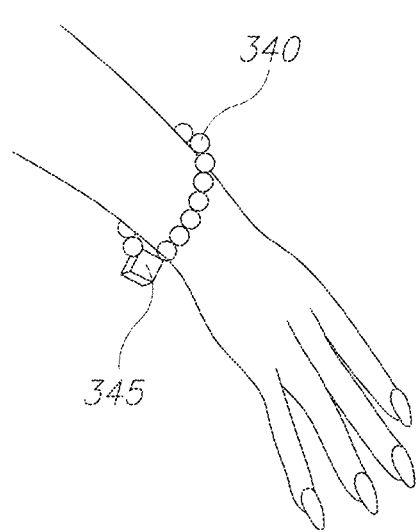

Referring now to FIG. 3D, showing a dispenser embedded within a bracelet, in accordance with some exemplary embodiments of the disclosed subject matter. Dispenser 345 may be used as a part of a Bracelet 340 to apply scent on the user's wrist.

Figure 4:
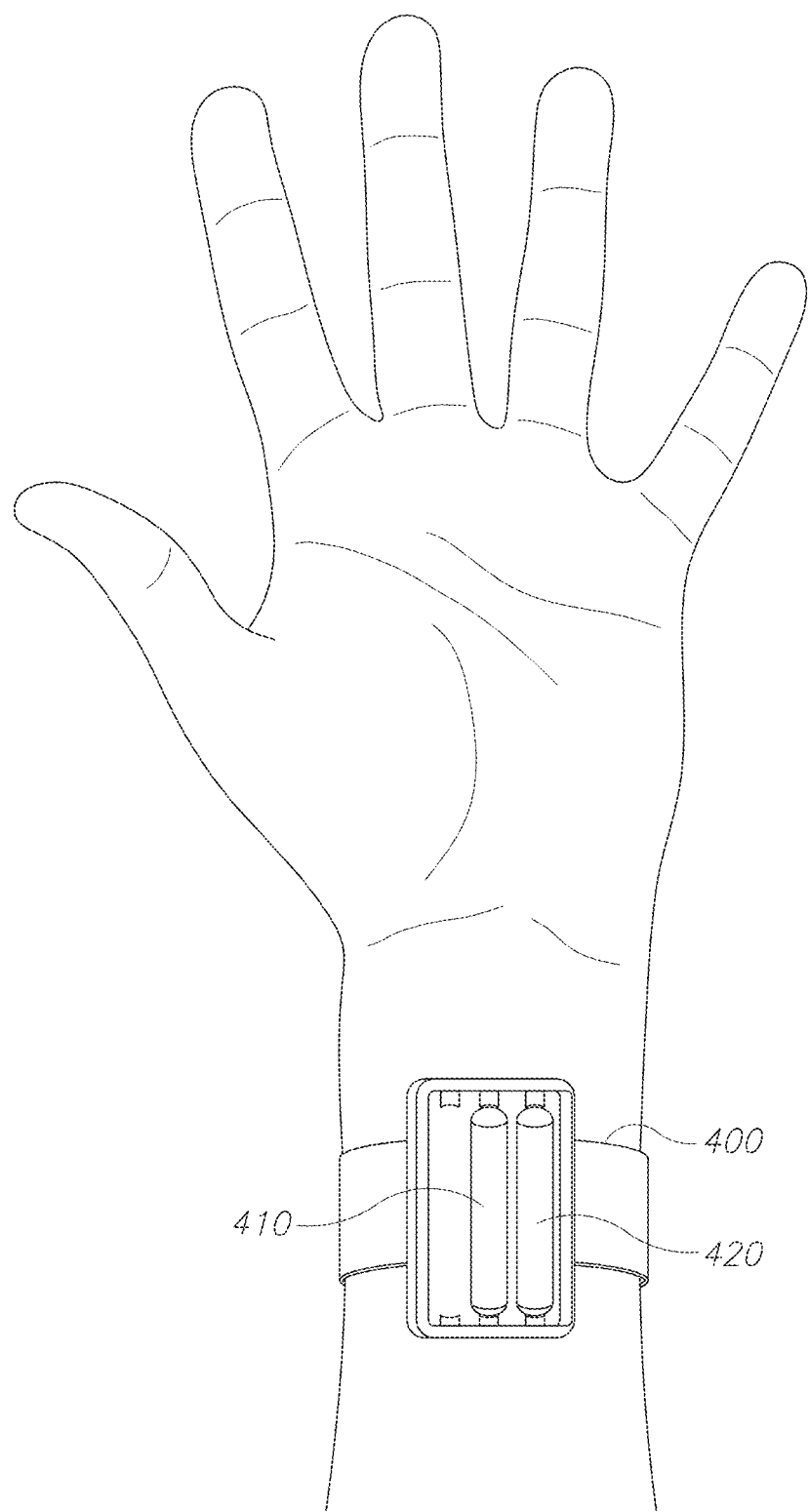
FIG. 4 shows an illustration of a device, in accordance with some exemplary embodiments of the disclosed subject matter.

Referring now to FIG. 4 showing a device, in accordance with some exemplary embodiments of the disclosed subject matter. A Device 400 may be an integrated dispenser-bracelet device.

In some exemplary embodiments, Device 400 may be a bracelet that can be worn on a user's wrist and may be configured to dispense a scent in accordance with the disclosed subject matter. Device 400 may be adapted to accommodate multiple cartridges, such as, Cartridges 410 and 420. In some exemplary embodiments, Device 400 may be configured to select a perfume from to be applied from the available cartridges. In some exemplary embodiments, the selection between the available cartridges may be performed based on a determination by a scent determinator, such as 240 of FIG. 2.

In some exemplary embodiments, each one of the Perfume Cartridges 420 loaded into Dispenser 400 may contain perfume of a different top note scent. In some exemplary embodiments, each scent may be associated with a different event and may be applied in response to an occurrence of the associated event. In some exemplary embodiments, Cartridge 420 may be a disposable cartridge, a refillable cartridge, or the like.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of program code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As will be appreciated by one skilled in the art, the disclosed subject matter may be embodied as a system, method or computer program product. Accordingly, the disclosed subject matter may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present invention may take the form of a computer program product embodied in any tangible medium of expression having computer-usable program code embodied in the medium.

Any combination of one or more computer usable or computer readable medium(s) may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CDROM), an optical storage device, a transmission media such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to wireless, wireline, optical fiber cable, RF, and the like.

Computer program code for carrying out operations of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A method comprising:
    detecting an event, wherein the event is associated with a user and with an approaching person, wherein said detecting comprises receiving readings regarding the approaching person from a sensor;
    in response to the event, determining, by a processor, a characterization of the approaching person based on the readings regarding the approaching person;
    determining a personalized scent for the event, the personalized scent is based on the characterization of the approaching person; and
    applying the personalized scent on the user to fragrance the user with the personalized scent prior to an encounter of the user with the approaching person, said applying is to enable the approaching person to sense the personalized scent during the encounter.

2. The method of claim 1, wherein said determining comprises: performing facial recognition to identify the approaching person, wherein the user is about to physically encounter the approaching person, wherein the personalized scent is determined based on the identity of the approaching person.

3. The method of claim 1, wherein the characterization is selected from the group consisting of: a gender of the approaching person; an identity of the approaching person; an age of the approaching person, and a demographic profile of the approaching person.

4. The method of claim 2, wherein said performing facial recognition comprises determining whether the approaching person is a female or a male, and wherein said determining the personalized scent provides a different scent for a female than for a male.

5. The method of claim 1, wherein said detecting the event is performed using a location sensor.

6. The method of claim 1, wherein the event comprises a gesture of the user.

7. The method of claim 6, wherein the gesture is a part of a non-verbal greeting between the user and the approaching person.

8. The method of claim 1, wherein said applying comprises applying, by a dispenser, a perfume having the personalized scent.

9. The method of claim 1, wherein said applying the personalized scent comprises applying a perfume having the personalized scent, wherein the perfume consists of a top note.

10. The method of claim 1, wherein said applying is purposely triggered by the user.

11. The method of claim 1, wherein said applying comprises transmitting an instruction to a dispensing component; in response to the instruction, the dispensing component applying the personalized scent on the user.

12. The method of claim 1, wherein said detecting the event comprises performing facial recognition to characterize the approaching person, wherein the personalized scent is determined based on the characterization of the approaching person, whereby applying different scents in response to different approaching people.

13. The method of claim 1, wherein said applying the personalized scent comprises applying a perfume having the personalized scent, wherein the perfume having evaporating coefficient of between 1 and 14.

14. A system comprising:
- a detecting component configured to detect an event associated with a user and an approaching person, wherein said detecting component is coupled with a sensor that is configured to provide readings regarding the approaching person;
- a processor configured to determine, in response to the event, a characterization of the approaching person based on the readings regarding the approaching person;
- a scent determinator configured to determine a personalized scent for the event, the personalized scent is based on the characterization of the approaching person; and
- a dispenser configured to apply the personalized scent on the user to fragrance the user with the personalized scent prior to an encounter of the user with the approaching person, said applying is to enable the approaching person to sense the personalized scent during the encounter.

15. The system of claim 14, wherein said detecting component is operatively coupled with a location sensor, wherein said scent determinator is configured to determine the personalized scent based on a location determined by said location sensor.

16. The system of claim 14, wherein said scent determinator comprises a facial recognition component operatively coupled with a camera, wherein said facial recognition component is configured to characterize the approaching person, wherein the user is about to physically encounter the approaching person, wherein the personalized scent is determined based on the characterization of the approaching person.

17. The system of claim 16, wherein the camera is a camera of an augmented reality glasses worn by the user.

18. The system of claim 14, wherein said detecting component is embedded in an augmented reality glasses worn by the user.

19. The system of claim 14, wherein said dispenser is embedded within a wearing item, wherein the wearing item is selected from the group consisting of: an item worn in proximity to a neck of the user and an item worn by the user in proximity to a wrist of the user.

20. The system of claim 19, wherein the wearing item is selected from the group consisting of: a bracelet; a tie; a cufflink; a scarf; a jewelry pin; a collar and a necklace.

21. The system of claim 14, wherein said scent determinator and said dispenser are physically separated.

22. A perfume cartridge comprising a container holding a perfume, wherein said cartridge is configured in size and shape to be loaded to the system of claim 14, wherein said dispenser is configured to apply the personalized scent by dispensing the perfume from said container.

\* \* \* \* \*